United States Patent [19]

Slaugh

[11] Patent Number: 4,962,267

[45] Date of Patent: Oct. 9, 1990

[54] DOUBLE BOND ISOMERIZATION PROCESS

[75] Inventor: Lynn H. Slaugh, Cypress, Tex.

[73] Assignee: Shell Oil Company, Houston, Tex.

[21] Appl. No.: 285,577

[22] Filed: Dec. 16, 1988

[51] Int. Cl.$^5$ .............................................. C07C 5/23
[52] U.S. Cl. .................................................. 585/670
[58] Field of Search ....................................... 585/670

[56] References Cited

U.S. PATENT DOCUMENTS 4,255,605  3/1981  Dixon ................................. 585/644

*Primary Examiner*—Curtis R. Davis

[57] ABSTRACT

Higher carbon number olefins undergo double bond isomerization, essentially without skeletal rearrangement of the olefin molecules, upon contact with a catalyst comprising ruthenium oxide.

30 Claims, No Drawings

DOUBLE BOND ISOMERIZATION PROCESS

The present invention relates to a process for the isomerization of olefins, and more particularly to a process which effects isomerization of the double bond position in the olefin molecule without accompanying skeletal isomerization or olefin polymerization.

BACKGROUND OF THE INVENTION $C_4$ and higher olefins serve as a basic feedstock in the chemical industry for the synthesis of many important products, including, for instance, solvents, lubricants, detergents, and polymers. In each case, the reactivity of an olefin starting material for such a synthesis and/or the properties and performance of the resulting product may be strongly influenced by the particular structure, or mixture of structures, represented in the olefin. Thus, for example, detergents derived from linear olefins are as a rule substantially more biodegradable than corresponding detergents derived from olefins having multiple branches in their carbon structure, and the properties of polymers prepared from olefins are often greatly influenced by the position (alpha- or internal) of the double bond.

It is, in many cases, desirable to tailor the structure and/or the double bond position in a given olefin, to optimize its utility for conversion to products of interest. This is particularly true in various processes for the preparation of olefins having internal, rather than alpha, double bond position. The desired skeletal structure (commonly, but not exclusively, a linear structure) is typically obtained in an oligomerization process in which one or a mixture of lower carbon number olefins is converted into higher carbon number olefins. Of particular commercial importance is the oligomerization of ethylene to prepare higher carbon number, predominantly linear, alpha-olefins. Linear internal olefins are then prepared by double bond isomerization of the linear alpha-olefins.

Isomerization of higher carbon number alpha-olefins to internal olefins finds particular application in the process for the preparation of higher olefins from ethylene which is described in U.S. Pat. No. 3,647,906.

SUMMARY OF THE INVENTION

The present invention is directed to a process which achieves isomerization of the double bond position of a $C_4$ or higher olefin. It has been found that movement of the double bond in such an olefin, for instance, movement from an alpha- to an internal position in the molecule, is accomplished, essentially without any rearrangement of the olefin molecule's skeletal carbon structure, upon contact of the olefin with a catalyst comprising ruthenium oxide supported on alumina.

Accordingly, this invention provides a process for the double bond isomerization of an olefin feedstock comprising one or more $C_4$ or higher olefins, substantially without change in the olefins $\propto$ skeletal structure, which comprises contacting the olefin feedstock, under isomerization reaction conditions, with a catalyst comprising ruthenium oxide supported on alumina or silica.

In particularly preferred embodiments, the isomerization catalyst for the invention comprises a combination of the ruthenium oxide with a base, for instance, as the result of impregnation with an alkali metal or ammonium hydroxide.

In other preferred embodiments, the ruthenium oxide is supported on an alumina support, particularly an alumina support having a surface area in the range from about 50 to about 300 square meters per gram.

DETAILED DESCRIPTION OF THE INVENTION

The present invention is suitably applied to the isomerization of any olefin feedstock comprising one or more $C_4$ or higher carbon number olefins. The feedstock may contain one or a mixture of individual mono-olefins, which may be of linear or branched structure, and which may have alpha- or internal double bond position. From the standpoint of opportunities for commercial application, the feedstock preferably comprises in major part (i.e., 50% or more of the olefin molecules present) alpha-olefins. More preferably, at least about 70% of the olefin molecules are alpha-olefins, while a feedstock in which essentially all of the olefin molecules (i.e., at least about 90%) are alpha-olefins is considered most preferred. Further, for this same reason, preference is also expressed for an olefin feedstock in which at least about 50%, more preferably at least about 70%, and most preferably at least about 90% of the higher olefin molecules are of linear (straight-chain) carbon skeletal structure. Still further, the invention is preferably applied to an olefin feedstock wherein the individual mono-olefin(s) are in substantial part of a carbon number in the range from about 4 to 30, more preferably in the range from about 4 to 24 and most preferably in the range from about 10 to 18. A mixed carbon number olefin feedstock may, however, contain minor amounts of substantially higher carbon number olefins, for instance olefins having a carbon number of 100 or more.

The invention has particular utility in application for the isomerization of essentially linear alpha-olefins in the process described in the aforementioned U.S. Pat. No. 3,647,906. This patent describes a process having steps for the oligomerization of ethylene to produce a mixture of alpha-olefin oligomers having a broad range of carbon numbers, the isomerization of the oligomer mixture to internal olefins, and the disproportionation of the resulting internal olefins to maximize the production of olefins in the intermediate (e.g., $C_{10}$ to $C_{18}$) carbon number range. The process of this invention is very suitable for the purposes of the isomerization step in the process of U.S. Pat. No. 3,647,906. The teachings of this patent are incorporated herein by this reference.

For purposes of this invention, the olefin feedstock is contacted under isomerization reaction conditions, with a specified heterogeneous catalyst, comprising ruthenium oxide supported on alumina.

The olefin feedstock is suitably in either liquid or gaseous form during contact with the catalyst, depending on carbon numbers of the olefins present, process temperature and pressure conditions, and the possible presence of a process solvent. Temperature conditions for the isomerization are generally in the range from about 0° to 500° C. Process temperature preferably exceeds about 80° C for a process of meaningful isomerization reaction rate, while a temperature below about 250° C. is preferred in order to minimize side reactions, such as olefin dimerization. Temperatures in the range of about 100° to 200° C. are typically more preferred, and those in the range of about 125° to 200° C. are considered most preferred. Process pressure is not critical to the invention, and can vary over a broad range, e.g., 0.1 to 2000 psia. Atmospheric or greater pressure is generally most convenient, while preference can be expressed for pressures of between about 0 and 1000 psig. Olefin feedstocks wherein the olefins present have average carbon number up to roughly $C_{10}$ are typically present in vapor form under preferred conditions, while the higher carbon number olefin feedstocks are typically liquids.

The time of contact between the catalyst and the feedstock is likewise not critical to the process, and will depend upon the desired degree of isomerization, the composition of the olefin feedstock and the process temperature. Reaction times on the order of 5 minutes to 5 hours are typically sufficient. Contact can take place in any convenient manner, for instance, in either a fixed or fluid bed of the catalyst and in either a batch or continuous mode. When a flow of olefin is passed continuously over the catalyst, weight hourly space velocity is preferably in the range from about 0.2 to about 10, more preferably from about 2 to about 4.

The specified ruthenium oxide catalyst can be prepared under any of a variety of generally conventional procedures. For instance, in one preferred method, an alumina (or silica) support in particle form is impregnated with a solution of ruthenium oxide or, very suitably, another ruthenium compound (such as ruthenium nitrosyl nitrate, potassium hexacyanoruthenate, ruthenium citrate, or ruthenium trichloride) which undergoes conversion to ruthenium oxide upon heating in an oxygen-containing atmosphere. The impregnation solution contains a sufficient amount of the ruthenium compound to deposit between about 0.1 and 10%w of ruthenium on the support (calculated as ruthenium metal relative to finished, i.e., dried and calcined, catalyst). The impregnated material is then dried, for example at temperatures in the range from about 50° to 200° C., and calcined, for example at temperatures from about 300° to 900° C., preferably from about 300° to 700° C., and most preferably from about 400° to 650° C. in an oxygen-containing atmosphere. It is necessary that the ruthenium be in the form of the oxide in the finished catalyst. (Calcining the catalyst in a hydrogen atmosphere results in loss of isomerization activity.) Alternative methods of catalyst preparation, including, for example, dissolving the metal in hydrogen peroxide solution before impregnation of the support, will be apparent to those of skill in the art.

In particularly preferred embodiments, the isomerization catalyst for the invention is promoted by the presence of a base. Incorporation of the base into the supported ruthenium oxide catalyst provides a synergistic improvement in its isomerization activity. Most preferably, the base is an alkali metal oxide, present in a loading which represents about 0.05 to 3 times by weight, particularly about 0.2 to 2 times by weight, that of ruthenium. The base can be introduced into the catalyst, for example, by impregnating the alumina (or silica) with a solution which contains the base (or a precursor thereof) as well as the ruthenium compound. Generally, any compound which decomposes under catalyst calcination conditions (i.e., exposure to an oxygen-containing atmosphere at elevated temperature) to yield an alkali metal oxide is suitable as a precursor for purposes of incorporation of an alkali metal base component of the catalyst.

While the nature of the catalyst support is not narrowly critical to this invention, it is preferred that the necessary ruthenium and (when present) the optional base components be supported on a porous support, preferably an alumina support but also suitably a silica support, having a surface area in the range from about 50 to about 300 square meters per gram, more preferably in the range from about 100 to about 250 square meters per gram. Embodiments of the invention utilizing a gamma alumina support are particularly preferred.

Very effective isomerization performance has been observed for catalyst loadings of ruthenium in the range from about 0.5 to about 5%w and of base in the range from about 0.2 to about 2.5%w, in each case calculated on the basis of ruthenium metal (or alkali metal) relative to total dry catalyst weight. Catalyst loadings of about 1 to 3%w ruthenium and about 0.3 to 2%w base (calculated on this same basis) are considered preferred.

If the process of the invention is carried to completion, i.e., equilibrium, the product is a mixture of double bond positional isomers, consisting essentially of internal olefins, characterized by a largely random distribution of the double bond position. The invention is largely intended for (but not limited only to) application for the isomerization of a feedstock containing substantial amounts of alpha-olefins to a corresponding mixture of internal olefins.

The process achieves isomerization of the olefin molecule's double bond position, without significant skeletal rearrangement of the olefin's carbon structure, and also without promoting significant dimerization or other polymerization of the olefins. Both dimerization and skeletal isomerization are recognized as problems in conventional double bond isomerization processes.

The invention is further described with reference to the following examples, which are intended to illustrate certain preferred embodiments of the invention, without limiting its broader scope.

EXAMPLE 1

For preparation of a supported ruthenium oxide catalyst, 2 grams of ruthenium(IV) oxide, $RuO_2 \cdot XH_2O$, was dissolved in 30 grams of distilled water. The resulting solution was impregnated into 30 grams of an alumina support (Kaiser K-101, characterized as a gamma alumina having a surface area of 209 square meters per gram). For purposes of impregnation, just enough of the metal salt solution was used to fill the pores of the support. After drying at 60° C. for one half hour, the impregnated material was calcined in a flow of air from 25° to 100° C. for one hour and then in a flow of air at 550° C. for another two hours. The resulting catalyst contained 1.78%w ruthenium, calculated on the basis of the metal.

This catalyst was applied to illustrate the isomerization, according to the process of the invention, of an feedstock comprising alpha-olefin(s), in this case a feedstock consisting essentially of 1-hexene. The alumina-supported ruthenium oxide catalyst (5 grams), was packed into a Vycor glass tube flow reactor. A flow of 20 ml per hour of the 1-hexene was vaporized, mixed with a nitrogen diluent (6 ml per minute), and passed over the catalyst. Weight hourly space velocity, calculated on the basis of the 1-hexene feedstock, was 2.7. The reactor was maintained at 150° C. and essentially atmospheric pressure. In a product sample obtained after 0.5 hours under these conditions, 42.2% of the 1-hexene had been converted to internal hexenes.

EXAMPLES 2-8

To illustrate the beneficial effect of incorporating a base in the alumina supported ruthenium oxide catalyst, a series of catalysts were prepared by impregnating the K-101 alumina with different amounts of ruthenium oxide and potassium hydroxide.

For examples 2-5, alumina supported ruthenium oxide catalyst prepared as described in example 1 was further impregnated with a base by adding a water solution of potassium hydroxide. The potassium impregnated catalyst was then dried and recalcined in the same manner described in example 1. The loading of base on the final catalyst was varied between 0.26%w and 3.42%w, calculated on the basis of potassium present.

For examples 6-8, catalyst was prepared with an increased ruthenium oxide loading of 3.39%w, calculated on the basis of ruthenium present. Different amounts of base were then incorporated into this catalyst in the manner described above.

Each of the resulting catalysts was evaluated for its 1-hexene isomerization activity, applying the reactor and reaction procedures and conditions described in example 1. Results are shown in the following table, for samples obtained after 0.5 hour in examples 2-5 and for samples obtained after 3.0 hours in examples 6-8.

| Example No. | Ru % w | K % w | % 1-hexene Isomerization |
|---|---|---|---|
| 2 | 1.78 | 0.26 | 76.4 |
| 3 | 1.78 | 0.51 | 86.7 |
| 4 | 1.78 | 1.23 | 82.6 |
| 5 | 1.78 | 3.42 | 63.6 |
| 6 | 3.39 | 1.21 | 50.3 |
| 7 | 3.39 | 2.29 | 69 |
| 8 | 3.39 | 3.92 | 25 |

The feedstock olefins and the product olefins were analyzed by GLC techniques to determine the amount of branching in the hexene molecules (after hydrogenation). The feedstock was found to contain about 1.2-1.3% branched olefins, which was (within experimental error) the same degree of branching detected in the products.

COMPARATIVE EXPERIMENT A

In order to illustrate the synergism between the ruthenium oxide and the base components of preferred catalysts of the invention, a process was carried out (not in accordance with the invention) in which potassium hydroxide (KOH) alone was supported on alumina and tested for its ability to catalyze the isomerization of 1-hexene. The following table presents the results of this comparative experiment, in comparison with the results of preceding examples 1 and 4.

| Example or Experiment No. | Ru % w | K % w | % 1-hexene Isomerization |
|---|---|---|---|
| A | 0.0 | 1.5 | 9.3 |
| 1 | 1.78 | 0.0 | 42.2 |
| 4 | 1.78 | 1.23 | 82.6 |

EXAMPLES 9-11

A series of alumina supported ruthenium oxide and base catalysts were prepared according to the general procedures of Examples 1 and 2-8. However, in each case, the alumina was impregnated with an aqueous solution of ruthenium nitrosyl nitrate, $Ru(NO)(NO_3)_3$. Different bases, e.g., potassium hydroxide (KOH), sodium hydroxide (NaOH), and lithium hydroxide (LiOH), were incorporated into the different catalysts by impregnation with aqueous solutions. Although the amounts of KOH, NaOH and LiOH vary on a weight basis, each represents and approximately equal amount of alkali metal, on the basis of the number of alkali metal atoms present.

The resulting catalysts were evaluated for isomerization activity, applying the same reactor, procedures and conditions as described in example 1. Results for 1-hexene isomerization in these examples are presented in the following table. Time of sampling indicated hours after the reaction was commenced.

| Example No. | Ru % w | Alkali Metal | Alkali Metal % w | Time Sampled (Hours) | % 1-hexene Isomerization |
|---|---|---|---|---|---|
| 9 | 2.2 | K | 1.3 | 0.5 | 93.2 |
| 10 | 2.2 | Na | 0.69 | 1 | 93.6 |
|  |  |  |  | 2 | 93.3 |
| 11 | 2.2 | Li | 0.15 | 1 | 95.4 |
|  |  |  |  | 2 | 95.8 |

EXAMPLE 12 AND COMPARATIVE EXPERIMENT B

The catalyst of example 4 was prepared under procedures which included heating of the ruthenium oxide impregnated alumina in flowing air programmed for a temperature rise to 100° C. over a period of 1 hour, followed by a rise to a final temperature of 550° C. over another 2 hour period. The resulting catalyst was highly active for the desired isomerization.

Comparative experiment B illustrates that a catalyst prepared by heating in a hydrogen (reducing) atmosphere has little isomerization activity. For this purpose, the catalyst of example 4 was contacted with a 12 cc per minute flow of a 50:50 mixture of hydrogen and nitrogen at a temperature programmed to rise to 100° C. in 1 hour and to 300° C. over another 2 hours.

For example 12, the active oxide catalyst was regenerated from the catalyst of comparative experiment B upon contact with air at a temperature which rose to 100° C. over 1 hour and then to 550° C. over an additional 2 hour period.

The catalysts of comparative experiment B and example 12 were evaluated for isomerization activity, using the reactor and reaction procedures and conditions described in example 1. The results follow, together with reference for comparison to the results of example 4.

| Example or Comparative Experiment No. | % 1-hexene Isomerization |
|---|---|
| 4 | 82.6 |
| B | 10.0 |
| 12 | 94.8 |

These examples and comparative experiment demonstrate the criticality of the use of a ruthenium oxide catalyst. This is considered particularly surprising in view of observations that certain other supported metal isomerization catalysts are necessarily reduced to increase isomerization activity.

I claim as my invention:

1. A process for the double bond isomerization of an olefin feedstock comprising one or more C4 or higher mono-olefins, which comprises contacting the feedstock under isomerization conditions with a catalyst comprising ruthenium oxide and an alkali metal oxide on an alumina support.

2. The process of claim 1, wherein the catalyst comprises from about 0.5 to about 5 percent by weight of ruthenium and from about 0.2 to about 2.5 percent by weight of alkali metal.

3. The process of claim 1, wherein the catalyst comprises alkali metal in an amount by weight which is between about 0.1 and 3 times the amount of ruthenium present in the catalyst.

4. The process of claim 2, wherein the catalyst comprises alkali metal in an amount by weight which is between about 0.1 and 3 times the amount of ruthenium present in the catalyst.

5. The process of claim 1, wherein the alumina support has a surface area in the range from about 50 to about 300 square meters per gram.

6. The process of claim 2, wherein the alumina support has a surface area in the range from about 50 to about 300 square meters per gram.

7. The process of claim 3, wherein the alumina support has a surface area in the range from about 50 to about 300 square meters per gram.

8. The process of claim 4, wherein the alumina support has a surface area in the range from about 50 to about 300 square meters per gram.

9. The process of claim 4, wherein the catalyst comprises from about 1 to about 3 percent by weight of ruthenium and from about 0.3 to about 2 percent by weight of alkali metal, and the weight of alkali metal present is between about 0.1 and 3 times that of the ruthenium.

10. The process of claim 9, wherein the alumina support has a surface area in the range from about 50 to about 300 square meters per gram.

11. The process of claim 10, wherein the alumina support has a surface area in the range from about 100 to about 250 square meters per gram.

12. The process of claim 1, wherein the olefin feedstock comprises in major part one or more alpha-olefins in the carbon number range from 4 to about 30.

13. The process of claim 12, wherein the isomerization conditions comprise a temperature in the range from about 80 to about 250° C. and a pressure in the range from about 0.1 to about 1000 psia.

14. The process of claim 13, wherein the olefin feedstock consists essentially of alpha-olefins in the carbon number range from about 4 to about 30.

15. The process of claim 14, wherein at least about 70% of the olefins in the olefin feedstock have a linear skeletal structure.

16. The process of claim 15, wherein the catalyst comprises from about 1 to about 3 percent by weight of ruthenium and from about 0.3 to about 2 percent by weight of alkali metal, and the weight of alkali metal present is between about 0.1 and about 3 times that of the ruthenium.

17. The process of claim 16, wherein the alumina support has a surface area in the range from about 50 to about 300 square meters per gram.

18. A process for the double bond isomerization of an olefin feedstock consisting essentially of one or more $C_4$ or higher mono-olefins, which comprises contacting the feedstock under isomerization conditions with a catalyst comprising ruthenium oxide and an alkali metal oxide on a gamma-alumina support having a surface area between about 100 and about 250 square meters per gram.

19. The process of claim 18, wherein the catalyst comprises from about 1 to about 3 percent by weight of ruthenium and from about 0.3 to about 2 percent by weight of alkali metal, and the weight of akali metal present is between about 0.2 and about 2 times that of the ruthenium.

20. The process of claim 19, wherein the isomerization conditions comprise a temperature in the range from about 80 to about 250° C. and a pressure in the range from about 0.1 to about 1000 psia.

21. The process of claim 20, wherein the olefin feedstock consists essentially of linear alpha-olefins, substantially in the carbon number range from about 4 to about 30.

22. A process for the double bond isomerization of an olefin feedstock comprising one or more $C_4$ or higher mono-olefins, which comprises contacting the feedstock under isomerization conditions with a catalyst prepared by a process which comprises impregnating an alumina support with a solution of a ruthenium compound and with a solution of a base and calcining the impregnated support in an oxygen-containing atmosphere.

23. The process of claim 22, wherein the alumina support is impregnated with sufficient ruthenium compound solution to deposit between about 0.1 and 10%w of ruthenium on an alumina support (calculated as ruthenium metal, relative to weight of the calcined catalyst).

24. The process of claim 23, wherein the base is an alkali metal oxide.

25. The process of claim 23, wherein the alumina support has a surface area in the range from about 50 to about 300 square meters per gram.

26. The process of claim 25, wherein the catalyst comprises from about 0.5 to about 5 percent by weight of ruthenium and from about 0.2 to about 2.5 percent by weight of alkali metal.

27. The process of claim 26, wherein the olefin feedstock comprises in major part one or more alpha-olefins.

28. The process of claim 27, wherein the olefins feedstock comprises in major part one or more alpha-olefins in the carbon number range from 4 to about 30.

29. The process of claim 28, wherein the isomerization conditions comprise a temperature in the range from about 80 to about 250° C. and a pressure in the range from about 0.1 to about 1000 psia.

30. The process of claim 29, wherein the catalyst comprises alkali metal in an amount by weight which is between about 0.1 and 3 times the amount of ruthenium present in the catalyst.

* * * * *